United States Patent [19]

Johnson et al.

[11] Patent Number: 4,716,256

[45] Date of Patent: Dec. 29, 1987

[54] HYDROGENATION OF DIENES

[75] Inventors: Marvin M. Johnson; Gerhard P. Nowack, both of Bartlesville, Okla.

[73] Assignee: Phillips Petroleum Company, Bartlesville, Okla.

[21] Appl. No.: 696,971

[22] Filed: Jan. 31, 1985

[51] Int. Cl.$^4$ .................................................. C07C 5/02
[52] U.S. Cl. ..................... 585/274; 585/277; 585/259; 208/144; 208/145
[58] Field of Search ............ 585/274, 277, 259; 502/167; 208/144, 145

[56] References Cited

U.S. PATENT DOCUMENTS

| | | | |
|---|---|---|---|
| 2,576,743 | 11/1951 | Allenby | 585/274 |
| 3,041,385 | 6/1962 | Bourne et al. | 585/259 |
| 3,444,256 | 5/1969 | Engelhard et al. | 585/259 |
| 4,131,627 | 12/1978 | Wideman | 585/274 |
| 4,155,943 | 5/1979 | Ofstead et al. | 585/274 |
| 4,161,483 | 7/1979 | Cahen | 502/167 |
| 4,188,348 | 2/1980 | Menapace | 585/274 |

*Primary Examiner*—Curtis R. Davis
*Assistant Examiner*—Chung K. Pak
*Attorney, Agent, or Firm*—J. E. Phillips

[57] ABSTRACT

Process for the selective hydrogenation of diolefinic compounds to monoolefinic compounds employing catalyst consisting essentially of elemental nickel on an inorganic support in the presence of hydrogen and at least one nitrogen-containing compound is disclosed. Selective hydrogenation of the less substituted of the two carbon-carbon double bonds of the diolefinic compound is achieved while isomerization of the more highly substituted, non-hydrogenated double bond, is minimized.

9 Claims, No Drawings

HYDROGENATION OF DIENES

BACKGROUND OF THE INVENTION

This invention relates to hydrogenation of diolefinic compounds. In one aspect, the invention relates to the selective hydrogenation of diolefinic compounds to produce monoolefinic compounds.

In the hydrogenation of diolefins, it is sometimes desired to selectively saturate one, but not both, of the diolefin double bonds in order to produce monoolefin products. In addition, it is sometimes desired to avoid isomerization of the remaining double bond in the product monoolefin. Although processes and catalysts capable of the desired selectivity are known in the art, there is still room for improvement. Thus, selective hydrogenation processes which employ catalysts which are less expensive than known selective hydrogenation catalysts such as alumina-supported platinum as well as selective hydrogenation processes which employ cataysts which are less susceptible to poisoning by feed impurities than are prior art catalysts are desired.

OBJECTS OF THE INVENTION

An object of the invention, therefore, is the selective hydrogenation of diolefins to produce monoolefins, wherein isomerization of the residual double bond in the monoolefin product is minimized.

Another object of the invention is a process for the selective hydrogenation of diolefins to produce monoolefins employing an inexpensive catalyst which is not susceptible to poisoning by feed impurities.

These and other objects and advantages of the invention will be apparent from the detailed description of the invention and the appended claims.

STATEMENT OF THE INVENTION

We have discovered that the selectivity for the hydrogenation of diolefins to monoolefins with minimum isomerization of the remaining double bond of the monoolefin product can be greatly increased by contacting the diolefin with hydrogen and a supported nickel catalyst in the further presence of at least one nitrogen-containing compound.

DETAILED DESCRIPTION OF THE INVENTION

In accordance with the present invention, a process for the selective hydrogenation of diolefinic compounds to produce monoolefinic compounds is provided which comprises contacting a diolefinic compound with hydrogen, at least one nitrogen-containing compound and a supported nickel catalyst under reaction conditions which are suitable to produce a monoolefinic compound.

Catalysts

The supported nickel catalysts employed in the practice of the present invention consist essentially of elemental nickel on an inorganic support and may be prepared by various methods known to those skilled in the art. For example, catalysts may be conveniently compared by contacting at least one nickel compound in the presence of inorganic oxide support. The conditions under which catalyst components are contacted are not critical. Thus, techniques such as, for example, slurry techniques, solution techniques, and the like may be employed. After the catalyst components have been thoroughly blended, solvent, if employed, can be removed by evaporation. Catalyst can then be calcined as desired to remove solvent and nickel counterions, and to convert nickel to the oxide form. Finally, the nickel deposited on the inorganic support can be converted to the elemental form by a reducing treatment such as, for example, heating in the presence of a hydrogen containing atmosphere.

Suitable nickel compounds for use in the preparation of supported elemental nickel on inorganic support are compounds which are convertible, via the oxide, to the elemental form in the presence of a hydrogen containing atmosphere. Exemplary nickel compounds include, but are not limited to, nickel formate, nickel acetate, nickel hydroxide, nickel nitrate, nickel acetylacetonate and the like, and mixtures of any two or more thereof.

The term inorganic support is intended for purposes of this disclosure to include those support materials which are useful for the preparation of heterogeneous catalysts. Suitable support materials include, but are not limited to, silica, alumina, silica-alumina, aluminum phosphate, zirconium phosphate, titanium phosphate, calcium phosphate, magnesium phosphate, activated carbon, magnesia-titania, thoria, titania, zirconia, and the like, as well as mixtures of any two or more thereof. Silica and alumina are presently preferred supports because of their ready availability, ease of handling, and resultant good activity of catalysts prepared with such supports.

The proportion of element nickel combined with the support can vary appreciably, but generally the support will contain at least about 1% by weight of nickel metal, based on the total weight of support plus nickel metal. Generally, the support will contain an upper limit of about 40% by weight of nickel metal, based on the total weight of support plus nickel metal. Amounts of about 2 to about 20% by weight of nickel metal, based on the total weight of support plus nickel metal are preferred, with amounts ranging from about 5 to 10% by weight of nickel metal based on the total weight of support plus nickel metal are especially preferred because excellent catalyst reactivities and product selectivities are obtained.

Nitrogen-Containing Compound

Any suitable nitrogen compound may be utilized as the nitrogen-containing compound utilized in the process of the present invention. Examples of suitable nitrogen compounds include ammonia, and primary, secondary and tertiary amines having the following formula:

$NR_3$, 

wherein each R is independently H, a $C_1$ up to about $C_{10}$ alkyl or a $C_5$ up to about $C_{10}$ cycloalkyl or aromatic radical. Additional nitrogen containing compounds contemplated to be within the scope of the present invention include heterocyclic nitrogen compounds as well as alkyl derivatives thereof, inorganic nitrogen compounds such as hydrazine and polyamine compounds such as ethylene diamine and hexamethylene diamine.

Examples of particular compounds which are included within the scope of the present invention include methylamine, ethylamine, n- or iso-propylamine, butylamine, cyclohexylamine, aniline, methylethylamine, dibutylamine, diamylamine, triethylamine, tripropylamine, tributylamine, pyridine, 2-methylpyridine, 4-methylpyridine, quinoline and isoquinoline.

Ammonia is the presently preferred nitrogen-containing compound for use in the process of the present invention. It is also presently preferred that the nitrogen-containing compound employed possess a volatility which is greater than the least volatile component of the reaction mixture containing the diolefinic compound so as to facilitate removal and recovery of the nitrogen-containing compound from the reaction mixture.

Substrate

The term diolefinic compound as employed herein is intended to include broadly organic molecules containing two carbon-carbon double bonds. Preferred diolefinic compounds for use in the process of the present invention have at least five up to about 30 carbon atoms and an unsymmetrical substitution pattern with respect to the double bonds, i.e., the first double bond is preferably more highly substituted than the second double bond of the diolefinic compound.

In accordance with the present invention, the rate at which the less substituted double bond is hydrogenated is significantly greater compared to the rate of hydrogenation of the more highly substituted double bond. In addition, isomerization of the non-hydrogenated double bond, i.e., the more highly substituted double bond, is minimized.

Example of diolefinic compounds included within the scope of the present invention include 4-vinylcyclohexene, which is selectively reduced to 4-ethylcyclohexene; isoprene, which can be selectively reduced to 2-methyl-1-butene; and the like.

The Process

Reaction parameters suitable for the practice of the present invention can be readily determined by those of skill in the art. For purposes of guidance, the following ranges are suggested. Although most any pressure can be employed, generally reaction pressure of about atmospheric up to about 5000 psig will be employed. Preferably, reaction pressures of about 10 to about 1000 psig will be employed. Suitable reaction temperatures include about 50° F. to about 400° F. with reaction temperature preferably maintained between about 100° and about 350° F. Reaction time can broadly be from a matter of minutes to a matter of hours. Generally, reaction time of about 30 minutes up to about 8 hours will be employed. In order to minimize the degree of hydrogenation of the more highly substituted double bond, an upper limit of about 120 minutes is preferred.

The total weight of catalyst to be used can be readily determined by one skilled in the art. Preferably, the amount of catalyst employed ranges from about 1 to 25 wt.% of the substrate charged. Most preferably, about 2 to 20 wt.% of catalyst is used, for most efficient use of catalyst and in order to achieve high product selectivities.

Substrate can be contacted with catalyst in the absence of solvent, or, if desired, substrate can be diluted with such solvents as saturated hydrocarbons having from about 4 up to about 20 carbon atoms, e.g., cyclohexane.

Where solvent is employed, the amount of solvent and substrate can be employed in any suitable ratio as readily determined by one skilled in the art. Since one fucntion of solvent is to aid in the removal of heat generated by the reaction, typically less solvent will be employed in a reactor having good heat transfer properties, while a relatively greater amount of solvent will be employed in a reactor having less efficient heat transfer properties. Suitable ratios are about 20:1 to about 1:5 parts by volume of solvent to substrate. Preferably, for ease of handling and product recovery, solvent and substrate are charged to the reactor in a volume ratio ranging from about 10:1 to about 1:2.

The process of the invention can be carried out by means of any apparatus whereby contact is achieved between the catalyst composition and the diolefinic compound to be hydrogenated. The process is in no way limited to the use of any particular apparatus. Thus, for example, the process of the invention can be carried out using a plug flow fixed bed reactor, a well stirred tank reactor or a series of well stirred tank reactors, a batch reactor of the like. Presently preferred is a batch reactor.

When the process of the invention is carried out employing a plug flow fixed bed reactor, any suitable flow rate for the substrate can be utilized. In general, the flow rate in terms of the volume of liquid per volume of catalyst per hour (LHSV) can range from about 0.1 up to about 20 and will more preferably range from about 0.5 up to about 5.

Those of skill in the art recognize that the extent of hydrogenation during the reaction can be controlled by adjusting several reaction parameters, such as, for example, by varying the reagent/catalyst mole ratio, the reagent/catalyst contact time, the reaction temperature, the reaction pressure and the like. By appropriate selection of reaction parameters, sufficient hydrogen can be provided so that hydrogenation of substantially all of one of the double bonds of the starting diolefin occurs while only minimum levels of hydrogenation of the second double bond occurs.

When the inventive hydrogenation reaction is carried out as a batch reaction, hydrogen is generally fed on demand, i.e., as it is taken up by the reaction mixture. Thus, for example, where reaction is carried out at 500 psig, this pressure will be maintained by continuously introducing more hydrogen. Preferably, the reaction is terminated when enough hydrogen has been provided to the reaction mixture to allow reduction of one double bond per diolefinic compound, i.e., one equivalent of hydrogen will be provided per equivalent of diolefinic compound. By this procedure, isomerization of the remaining double bond is minimized.

The nitrogen-containing compound is contacted with the catalyst and substrate in any suitable manner as known by those of skill in the art. Thus, catalyst can be pretreated with at least one nitrogen-containing compound, the nitrogen-containing compound may be provided to the reactor as a cofeed along with the substrate, the nitrogen-containing compound may be provided to the reactor as a second stream, nitrogen-containing compound may be provided intermittently to the reactor as a pulse, and the like. While suitable amounts of nitrogen-containing compound for use in the practice of the invention can be readily determined by those of skill in the art, generally about 0.01 to about 5 mole % of nitrogen containing compound based on the number of moles of diolefinic compound substrate will be employed.

The following non-limiting examples are presented to further illustrate the invention.

EXAMPLES

The general procedure for the selective hydrogenation of 4-vinylcyclohexene (4-VCH) involved placing 15 mL 4-vinylcyclohexene (4-VCH), 135 mL of pure cyclohexane and about 2.3 grams of a Ni/SiO$_2$ catalyst in a stirred autoclave of 300 cc capacity. The autoclave was pressured to 300 psig with H$_2$ gas and vented several times so as to remove air. Then the reactor was pressured to about 500 psig H$_2$, and the temperature was raised to the desired reaction temperature while the reactor contents were stirred. Samples were withdrawn by opening a valve for a short period of time and analyzed by gas liquid chromatography (GLC).

EXAMPLE I

The basic catalyst employed was prepared by impregnating Hi Sil ® silica (surface area: 140–160 m$^2$/g; PPG Industries, Pittsburgh, PA) with an aqueous solution of Ni(NO$_3$)$_2$, drying the impregnated material, and reducing it in a hydrogen stream at 370° C. for about 4 hours. The finished catalyst contained about 10 weight-% Ni.

Catalyst A

The above catalyst was re-reduced at about 370° C. for 20–60 minutes and allowed to cool under a hydrogen atmosphere to room temperature.

Catalyst B

Catalyst A was exposed to ammonia gas at atmospheric pressure for about 10–20 minutes before it was added to the autoclave.

Catalyst C

In an invention run (run 3; see Table I), ammonia gas was bubbled through the reactor containing 4-VCH and catalyst A until the vent gas turned litmus paper blue (i.e., the reactor contents were saturated with NH$_3$).

EXAMPLE II

This example illustrates the effect of NH$_3$ on the catalytic hydrogenation of 4-VCH in the presence of hydrogen and a Ni/SiO$_2$ control catalyst A or invention catalysts B or C, prepared in accordance with the procedure given in Example I. Pertinent reaction conditions and analysis results are summarized in Table I.

The following comparisons demonstrate the beneficial effect of the exposure of the Ni/SiO$_2$ catalyst to NH$_3$ on the selective hydrogenation of 4-vinylcyclohexene (4-VCH) to 4-ethylcyclohexene (4-ECH).

(1) Control run 1, 1 hour run time: 28% 4-VCH was left, i.e., 4-VCH conversion was 72%; selectively to 4-ECH was 54%; invention run 4, 2 hours run time: conversion of 4-VCH was also 72%; but, selectivity to 4-ECH was 83%. Thus, the selectivity to 4-ECH at essentially the same 4-VCH conversion was about 50% higher in invention run 4 than in control run 1.

(2) Invention run 3, 0–7 hours run time: the amount of cycloalkanes remained substantially constant, which indicates that essentially no new cycloalkanes were formed and about 85% 4-VCH was essentially completely converted to 4-ECH. This effect was not observed during the first two hours of control run 2, during which about 95% of 4-VCH was converted, yet the amount of cycloalkane in the product increased substantially (about 50%).

The examples have been provided merely to illustrate the practice of our invention and should not be read so as to limit the scope of our invention or the appended claims in any way. Reasonable variations and modifications, not departing from the essence and spirit of our invention, are contemplated to be within the scope of patent protection desired and sought.

We claim:

1. A process for the selective hydrogenation of 4-vinylcyclohexene to 4-ethylcyclohexene which comprises contacting said 4-vinylcyclohexene under hydrogenation conditions in the presence of hydrogen, a catalyst consisting essentially of elemental nickel on an inorganic support, and at least one nitrogen-containing compound; wherein said at least one nitrogen-containing compound is selected from the group consisting of:
pyridine,
2-methylpyridine,
4-methylpyridine,
quinoline,
isoquinoline,
hydrazine,
ethylene diamine,
hexamethylene diamine,
NR$_3$,
wherein each R is independently H, a C$_1$ up to about C$_{10}$ alkyl or a C$_5$ up to about C$_{10}$ cycloakyl or aromatic radical; and mixtures of any two or more thereof; and

TABLE I

| Run | Ni/SiO$_2$ Catalyst | NH$_3$ Present | Temp. (°F.) | Run Time (Hours) | 4-VCH | 4-ECH | 1-ECH | Cycloalkanes | Others |
|---|---|---|---|---|---|---|---|---|---|
| 1 (Control) | A | No | 71 | 0 | 99.0 | — | — | — | 0.9 |
|  | A | No | 82 | 1 | 27.9 | 39.8 | 2.7 | 27.7 | 2.1 |
|  | A | No | 70 | 2 | — | 0.1 | 0.3 | 99.7 | — |
| 2** (Control) | A | Traces | 71 | 0 | 57.2 | 2.1 | — | 40.2 | 0.4 |
|  | A | Traces | 80 | 2 | 2.9 | 32.9 | 2.8 | 59.5 | 2.0 |
|  | A | Traces | 79 | 5 | — | 13.1 | 2.3 | 84.4 | 0.1 |
| 3*** (Invention) | C | Yes | 71 | 0 | ~40 | ~3 | ~1 | ~55 | — |
|  | C | Yes | 79 | 4 | 25.3 | 19.0 | 0.6 | 53.0 | 2.1 |
|  | C | Yes | 79 | 7 | 5.8 | 37.4 | 1.0 | 52.6 | 3.2 |
| 4 (Invention) | B | Yes | 71 | 0 | 99.0 | — | — | — | 0.9 |
|  | B | Yes | 111 | 1 | 57.8 | 35.4 | 0.7 | 2.9 | 3.0 |
|  | B | Yes | 111 | 2 | 28.2 | 59.4 | 1.5 | 5.6 | 3.6 |
|  | B | Yes | 111 | 3 | 4.3 | 76.7 | 2.7 | 12.6 | 3.6 |

*4-VCH = 4-vinylcyclohexene
4-ECH = 4-ethylcyclohexene
1-ECH = 1-ethylcyclohexene
Cycloalkanes = mainly ethylcyclohexane plus some cyclooctane
**15 cc 4-VCH was added to completed run 1; then NH$_3$ was bubbled through the reactor for about 2 minutes
***15 cc 4-VCH was added to completed run 2; then NH$_3$ was bubbled through the reactor until vent gas turned litmus paper blue within the amount of said at least one nitrogen-containing compound ranges from about 0.01 up to 5 mole percent based on the moles of said 4-vinylcyclohexene.

2. A process is accordance with claim 1 wherein said inorganic support is selected from the group consisting of:
silica,
alumina,
silica-alumina,
aluminum phosphate,
zirconium phosphate,
titanium phosphate,
calcium phosphate
magnesium phosphate,
magnesia-titania,
thoria,
titania,
zirconia,
and mixtures of any two or more thereof.

3. A process in accordance with claim 1 wherein said inorganic support is silica.

4. A process in accordance with claim 1 wherein said inorganic support is alumina.

5. A process in accordance with claim 1 wherein said elemental nickel is present in a range of about 1 to 40 weight percent based on total weight of said support plus said elemental nickel.

6. A process in accordance with claim 1 wherein said contacting is carried out until about one equivalent of hydrogen is consumed per equivalent of 4-vinylcyclohexene charged charged.

7. A process in accordance with claim 1 wherein said contacting is carried out at a temperature of about 50° up to about 400° F. and a pressure of about atmospheric up to about 5000 psig.

8. A process in accordance with claim 1 wherein said contacting is carried out in the presence of at least one solvent selected from the group consisting of hydrocarbons having from about 4 to about 20 carbon atoms.

9. A process in accordance with claim 1 wherein said nitrogen-containing compound is ammonia.

* * * * *